(12) United States Patent
Kajita et al.

(10) Patent No.: US 6,479,732 B1
(45) Date of Patent: Nov. 12, 2002

(54) CDNA OF 4-COUMARATE: COENZYME A LIGASE AND PROCESS FOR MODIFYING LIGNIN IN PLANTS

(75) Inventors: Shinya Kajita, Tokyo (JP); Haruhiko Kawabata, Tokyo (JP)

(73) Assignee: Mitsubishi Paper Mills, Limited, Tokyo (JP)

( * ) Notice: Subject to any disclaimer, the term of this patent is extended or adjusted under 35 U.S.C. 154(b) by 0 days.

(21) Appl. No.: 09/556,312

(22) Filed: Apr. 24, 2000

(30) Foreign Application Priority Data

Apr. 23, 1999 (JP) .............................. 11-116784

(51) Int. Cl.⁷ ..................... A01H 5/00; C07H 21/04
(52) U.S. Cl. ................... 800/284; 800/278; 800/295; 800/298; 435/320.1; 435/410; 435/430; 536/24.5; 536/23.1
(58) Field of Search .............. 536/23.1, 24.5; 435/320.1, 410, 430; 800/298, 295, 278, 284

(56) References Cited

U.S. PATENT DOCUMENTS

| 5,451,514 A | 9/1995 | Boudet et al. ............ 435/172.3 |
| 5,850,020 A | 12/1998 | Blocksberg et al. ........ 800/205 |
| 5,952,486 A | 9/1999 | Bloksberg et al. ......... 536/23.6 |

FOREIGN PATENT DOCUMENTS

| EP | WO 98/11205 | 3/1998 | |
| EP | WO 99/10498 | 3/1999 | |
| EP | WO 99/31243 | 6/1999 | |
| EP | WO 00/22099 | 4/2000 | |
| JP | 9-173069 | 7/1997 | ........... C12N/15/09 |
| WO | 99/24561 | 5/1999 | ........... C12N/15/00 |

OTHER PUBLICATIONS

Kajita et al. Plant Cell Physiol. 37(7):957–965, 1996.*

* cited by examiner

*Primary Examiner*—W. Gary Jones
*Assistant Examiner*—Juliet Einsmann
(74) *Attorney, Agent, or Firm*—Sughrue Mion, PLLC

(57) ABSTRACT

The object of the present invention is to provide a transformed plant that produces woody raw materials having improved pulp cooking property and that has a growth characteristics equal to that of the wild type plant by changing the expression of 4-coumarate:coenzyme A ligase (4CL) gene.

By transforming a plant using an antisense 4CL gene or a sense 4CL gene constructed using a portion of cDNA encoding 4CL, it is possible to suppress the expression of the intrinsic 4C1 gene.

9 Claims, 1 Drawing Sheet

DIAGRAM OF T-DNA REGIONS ON BINARY VECTORS

ABBREVIATIONS:
NOSP, PROMOTER SEQUENCE OF NOPALINE SYNTHASE GENE
NPTII, CODING SEQUENCE OF NEOMYCIN PHOSPHOTRANSFERASE
T, TERMINATOR SEQUENCE OF NOPALINE SYNTHASE GENE
35SP, CAULIFLOWER MOSAIC VIRUS 35S PROMOTER
RB, RIGHT BOARDER SEQUENCE
LB, LEFT BOARDER SEQUENCE

SEQUENCE LISTING

<160> NUMBER OF SEQ ID NOS: 4

<210> SEQ ID NO 1
<211> LENGTH: 690
<212> TYPE: DNA
<213> ORGANISM: Eucalyptus globulus

<400> SEQUENCE: 1

```
gggacgacgg ggttgccgaa gggggtgatc ctgacgcacc gcaacctgat caccagcata      60
gcgcagcaag tggacggcga gaacccgaac ctccacctga gggcggagga cgtgatgctg     120
tgcgtgttgc cgctgttcca catctactcc ctcaacagcg tgctgctctg ctcgctccgc     180
gccgggcgg gagtgctgct gatgcacaag ttcgagatag ggacgttgct tcggctgatc      240
gagcgccacc gggtgtcggt ggccgcggtg gtgccacctc tggtgctggc cctggccaag     300
aaccccctgg tcgagaagtt cgacctctca tccatccgca tggtgctgtc aggggcggcg     360
ccgctgggca aggagctcga gctcgccctc cagacccgcc ttcccggagc catcttgggc     420
cagggatatg gaatgacgga agcgggaccg gtgctttcta tgtgcttggg gttcgccaag     480
caaccctttcc caaccaaatc gggttcgtgc gggacggttg ttcggaatgc agagctcaaa   540
gtcatcgacc ccgagaccgg ttcctcccctt ggctacaacc agcccggcga gatatgcatt   600
cgtggccaac aaattatgga aggatacctg aacgaccccg aggcgacttc gatcaccatt    660
gacacggatg gctggctgca cactggcgac                                      690
```

<210> SEQ ID NO 2
<211> LENGTH: 690
<212> TYPE: DNA
<213> ORGANISM: Eucalyptus globulus

<400> SEQUENCE: 2

```
gggacgacgg ggctgccgaa gggggtgatg ctcacgcaca ggggtcaagt gaccagcgtg      60
gcgcagcagg tcgacggaga caaccccaac ttgtacttcc acaaggagga cgtgatcctg     120
tgcacgctcc cgttgttcca catatactcc ctcaactcgg tgatgttctg cgcgctccgt     180
gtcggcgccg ccatcctgat catgcagaag ttcgagatcg tggcgctgat ggagctcgtg     240
cagcggtacc gggtgacggt cctgcccatc gtcccgccga tcgtgctggc gatcgccaag     300
agcgccgagg tggaccggta cgacctgtcg tcgatccgga ccatcatgtc gggtgcggtc     360
ccgatgggga aggagctcga ggacgccgtg cgagccaagc tgccgaatgc aagctcgga      420
cagggctatg ggatgacgga ggcaggcccg gtgctggcaa tgtgcctggc atttgcaaag    480
gagccgttcg agatcaagtc aggcgcgtgc gggaccgtcg tgaggaacgc ggagatgaag     540
atcgtcgacc cggagacagg ggcctcgctc ccgcggaacc aggccggcga gatctgcgtc     600
cggggtcacc agatcatgaa aggttatctg aacgaccccg aagcgaccgc taataccata     660
gacaaagaag ggtggctcca caccggcgat                                       690
```

<210> SEQ ID NO 3
<211> LENGTH: 23
<212> TYPE: DNA
<213> ORGANISM: Artificial Sequence
<220> FEATURE:
<223> OTHER INFORMATION: PCR Primer for amplification of partial
      cDNA fragments that encode 4-coumarate
<221> NAME/KEY: misc_feature
<222> LOCATION: (3)..(3)
<223> OTHER INFORMATION: "n" may be a, c, g, or t.

```
<221> NAME/KEY: misc_feature
<222> LOCATION: (6)..(6)
<223> OTHER INFORMATION: "n" may be a, c, g, or t.
<221> NAME/KEY: misc_feature
<222> LOCATION: (9)..(9)
<223> OTHER INFORMATION: "n" may be a, c, g, or t.
<221> NAME/KEY: misc_feature
<222> LOCATION: (12)..(12)
<223> OTHER INFORMATION: "n" may be a, c, g, or t.
<221> NAME/KEY: misc_feature
<222> LOCATION: (15)..(15)
<223> OTHER INFORMATION: "n" may be a, c, g, or t.
<221> NAME/KEY: misc_feature
<222> LOCATION: (18)..(18)
<223> OTHER INFORMATION: "n" may be a, c, g, or t.

<400> SEQUENCE: 3
ggnacnacng gnytnccnaa rgg                                          23

<210> SEQ ID NO 4
<211> LENGTH: 21
<212> TYPE: DNA
<213> ORGANISM: Artificial Sequence
<220> FEATURE:
<223> OTHER INFORMATION: PCR Primer for amplification of partial cDNA
      fragments that encode 4-coumarate
<221> NAME/KEY: misc_feature
<222> LOCATION: (4)..(4)
<223> OTHER INFORMATION: "n" may be a, c, g, or t.
<221> NAME/KEY: misc_feature
<222> LOCATION: (7)..(7)
<223> OTHER INFORMATION: "n" may be a, c, g, or t.
<221> NAME/KEY: misc_feature
<222> LOCATION: (13)..(13)
<223> OTHER INFORMATION: "n" may be a, c, g, or t.
<221> NAME/KEY: misc_feature
<222> LOCATION: (19)..(19)
<223> OTHER INFORMATION: "n" may be a, c, g, or t.

<400> SEQUENCE: 4
rtcnccngtr tgnarccanc c                                            21
```

CDNA OF 4-COUMARATE: COENZYME A LIGASE AND PROCESS FOR MODIFYING LIGNIN IN PLANTS

BACKGROUND OF THE INVENTION

The present invention relates to transformed plants obtained by constructing recombinant DNAs such as sense genes or antisense genes using CDNA that encodes 4-coumarate: coenzyme A ligase (hereinafter referred to as 4CL), an enzyme occurring in plants, and then introducing them into the genome to obtain the transformed plants.

In general, major building blocks of the cell wall of higher plants include, for example, lignin, a polymer compound having an aromatic nucleus, in addition to polysaccharides such as cellulose and hemicellulose. Lignin is known to deposit on the cell wall by the polymerization of cinnamyl alcohols biosynthesized from an essential amino acid phenylalanine of a living body via a plurality of enzymatic reactions. Lignin synthesized in the cell serves, in a sense, as a reinforcement for the maintenance of plant morphology together with polysaccharides, and it is being elucidated that it also plays an important role in the resistance to various stresses.

However, the presence of lignin, which is important for the maintenance of biological functions of plants, is not always welcome when materials in the plants are to be utilized as raw materials in various industries. In the pulping and paper making industry, for example, wood chips, construction waste wood, or unused residues derived from herbaceous plants and the like are used to produce pulp that makes a raw material for paper making. However, in many processes for pulp production, considerable amounts of energy and chemicals are used to remove lignin from wood materials. In the dairy industry too, grass and various plant residues are in common use as the fodder. In cases where the fodder taken up by domestic animals is digested in the digestive tract, it is known, lignin present in the fodder hinders its digestibility thereby reducing the efficiency of the fodder.

As one of the means to solve the above industrial problems associated with the presence of lignin, attempts have been made in the last few years to modulate the amount of lignin deposited on plant cell walls or the molecular structure of lignin using genetic manipulation. These attempts are intended to modify the functions for genes of enzymes involved in the biosynthesis of lignin to alter the amount of lignin formed in the cell wall and to alter the molecular structure of lignin. By facilitating changes in lignin biosynthesis using these methods, it is expected to be able to develop plants that have industrially advantageous properties.

For example, attention has been given to phenylalanine ammonia-lyase, an enzyme that catalyzes the initial reaction for synthesis of phenylpropanoid including lignin; in a transformed tabacco wherein the expression of the gene has been suppressed, it is stated, lignin content in plants is reduced and the relative amount of guaiacyl lignin is enhanced to that of syringyl lignin (Sewalt et al., Plant Physiology, vol 115, 41, 1997).

It has been reported that in a transformed Arabidopsis which expresses at a high level the gene of ferulate 5-hydroxylase, an enzyme thought to play an important role in the control of the relative amount of syringyl lignin in the entire lignin structure, the relative amount of syringyl lignin is enhanced (Chapple et al., Proc. Natl. Acad. Sci. U.S.A., vol 95, 6619, 1998).

U.S. Pat. No. 5,451,514 discloses, in an experiment employing transformed tabacco, that suppressing the expression of the gene of cinnamyl alcohol dehydrogenase (hereinafter referred to as CAD) involved in lignin monomer biosynthesis results in the modification of biosynthetic processes of phenolic compounds including lignin, thereby increasing the amount of lignin extracted from the cell wall associated with alkali treatment.

Furthermore, U.S. Pat. No. 5,850,020 and U.S. Pat. No. 5,952,486 disclose methods of reducing the lignin content in recombinant tabacco relative to that in the wild type plant, which method comprises isolating cDNAs of a plurality of enzymes related to lignin biosynthesis obtained from *Pinus radiata* and *Eucalyptus grandis*, and introducing recombinant DNA that uses these cDNAs into the genome of tabacco.

In addition to the above examples, the inventors of the present invention have disclosed in Japanese Unexamined Patent Publication (Kokai) No. 9-173069 that suppressing the expression of the 4CL gene that is a target gene of the present invention results in reduced lignin content in transformed tabacco and significant changes in the molecular structure of lignin. It has also been shown, however, that extremely abnormal growth occurs at a high frequency in transformed tabacco in which the expression of the gene has been suppressed (Kajita et al., 1996, Plant and Cell Physiology, 37, 957). If the modification of lignin in plants obtained by suppressing the expression of the 4CL gene is useful for industrial application, recombinant plants having such properties could develop an extremely abnormal growth, which would reduce the production efficiency of the plants themselves, and thereby, it is expected, would increase the total cost required in the processes from the cultivation of said plants to the production of final products. And therefore, their application into the industry in the art would be limited.

WO 99/24561 discloses a method which comprises suppressing the activity of the 4CL gene in aspen, thereby reducing the content of lignin present in the cell wall of the transformed aspen, and at the same time modifying the growth characteristics of the transformed aspen. It shows a similar effect to that of the present invention in that it reduced the lignin content in the cell wall, but it makes no mention of the characteristics of pulp production for wood chips obtained from the recombinant aspen.

On the other hand, Petit-Conil et al. conducted a pulping test using a transformed poplar in which the expression of the CAD gene had been suppressed. The result reveals that by using wood chips obtained from said transformed poplar, delignification is easier under the same condition than when using those obtained from the wild type plants (Proceedings of the 1998 7th International Conference on Biotechnology in the Pulp and Paper Industry, A37–A41, 1998). Although the result indicates that it is possible to obtain chip materials having excellent pulp productivity by modifying the function of the gene of enzymes involved in lignin monomer biosynthesis, the CAD gene noted by Petit-Conil et al. is entirely different from the 4CL gene noted in the present invention.

Thus, there has not been obtained at present a method of improving the characteristics as a raw material for pulp retained by woody substances containing lignin obtained from plants by modifying the expression of the endogenous 4CL gene to plants, and thereby modifying the lignin content or the molecular structure of lignin present in the plants.

It is an object of the present invention to provide transformed plants that offer woody substances more suitable for pulp production by modifying the content and the molecular structure of lignin deposited in the cell wall by modifying the expression of the 4CL gene.

SUMMARY OF THE INVENTION

As a result of intensive research in order to solve the above problems, the inventors of the present invention have successfully created transformed plants that exhibited decreased levels of 4CL activity. Furthermore, we have proved, based on the result of the pulping experiment using wood chips derived from these transformed plants, that the amount of pulp obtained from said plants is significantly high compared to that obtained from wild type plants when a delignification treatment was carried out to a similar degree to these plants, and thereby have completed the present invention.

Thus, the present invention relates to transformed plants that contribute to enhancing pulp productivity, and more specifically it relates to (1) CDNA of 4-coumarate:coenzyme A ligase having the nucleotide sequence as set forth in SEQ ID NO: 1, (2) CDNA of 4-coumarate:coenzyme A ligase having the nucleotide sequence as set forth in SEQ ID NO: 2, (3) a recombinant DNA having at least a portion of these cDNAs inserted in an antisense orientation to DNA containing any promoter and terminator sites, (4) a recombinant DNA having at least a portion of these CDNAs inserted in a sense direction to DNA containing any promoter and terminator sites, (5) a transformed plant obtained by introducing these recombinant DNAs into the genome, (6) a transformed plant in which the plant is a woody plant, (7) a transformed plant in which the woody plant is a plant of genus Eucalyptus, (8) cells obtained from these transformed plants, (9) seeds obtained from these transformed plants, (10) fruits obtained from these transformed plants, (11) a method of introducing the above recombinant DNA into the genome to change the production level of enzymes having a 4-coumarate:coenzyme A ligase activity, thereby changing the content of lignin present in the cell wall of the transformed plants, and (12) a method of introducing the above recombinant DNA into the genome to change the production level of enzymes having a 4-coumarate:coenzyme A ligase activity, thereby changing the molecular structure of lignin present in the cell wall of the transformed plants.

DETAILED DESCRIPTION OF THE INVENTION

Figure 1:
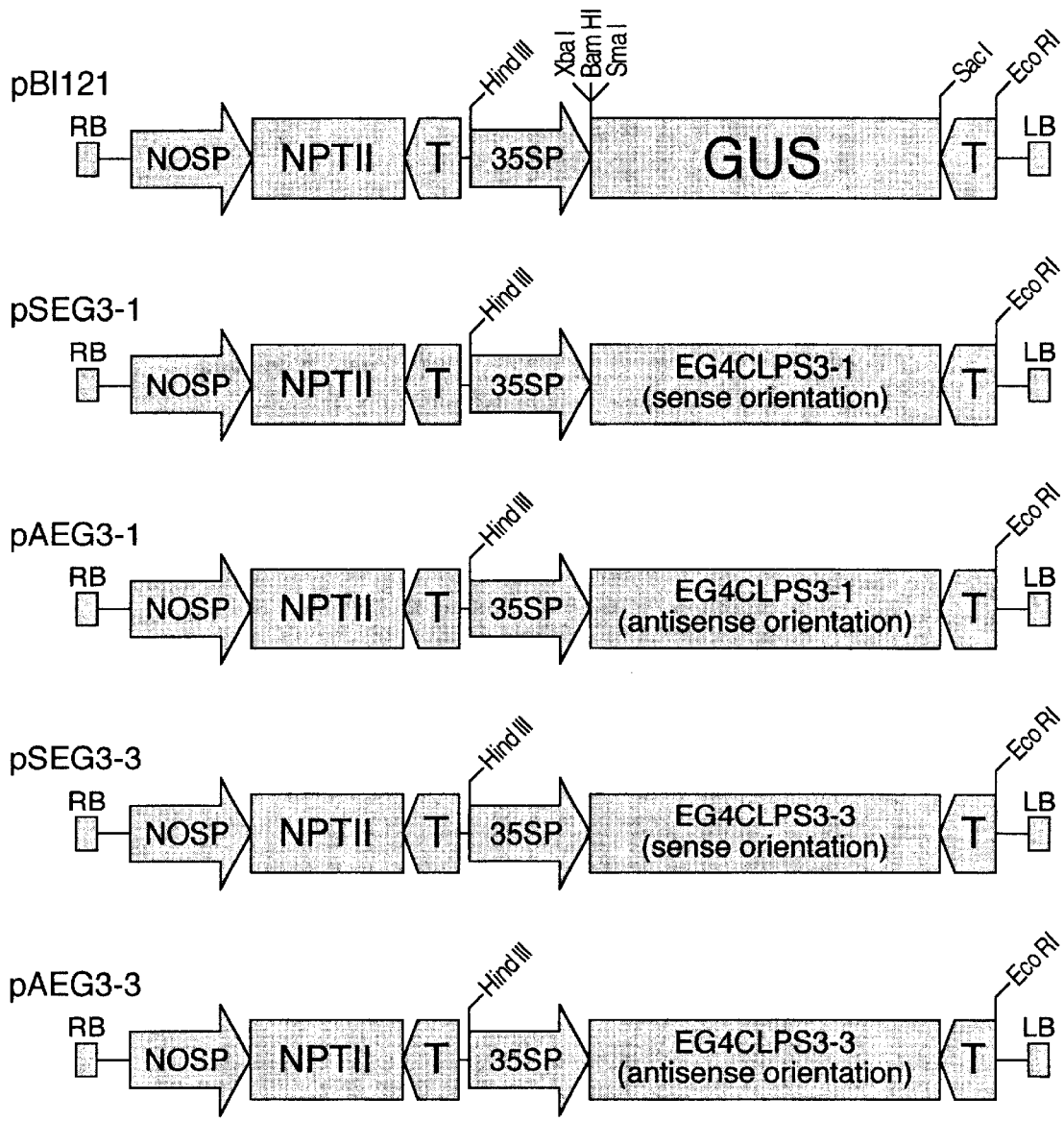
FIG. 1 shows the diagram of T-DNA regions on binary vectors.

The present invention, for the purpose of creating a transformed plant that contributes to enhanced pulp productivity, provides cDNA encoding the 4CL protein required, a recombinant DNA which is a combination of said DNA with a DNA having any promoter and terminator functions, and furthermore a method of creating a transformed plant using said recombinant DNA, and the present invention is composed of a transformed plant created by said method, cells, germ plasma, and seeds obtained from said plant.

As DNA encoding the amino acid sequence of 4CL for use in the present invention, there may be mentioned cDNAs and structural genes synthesized based on mRNA. Although these DNAs may be as they are obtained from any plant species, it is particularly preferred to use those obtained from a plant species included in the same genus as the transformed plant finally created. In constructing recombinant DNA to be introduced into the genome, the entire region of the cDNA or the structural gene or a portion thereof may be used, preferably a region carried by the cDNA is used and more preferably a region encoding the amino acid sequence of protein, among the cDNA region, is used. Although it is possible to use the nucleotide sequence of part of the cDNA and the structural gene that has been modified to another sequence, it is preferably used without modifying more than 60% or more of the original sequence.

As a gene to be introduced into the genome to control lignin content and the molecular structure of lignin, there may be mentioned an antisense gene or a sense gene constructed by combining the cDNA or the structural gene of 4CL with DNA having any promoter and terminator functions. Promoters used in constructing the gene to be introduced in the plant genome include, but not limited to, those that act potently in the cambium and the xylem cell region of plants, and there can be used promoters derived from the structural genes of enzymes involved in lignin biosynthesis including 4CL inherently arried by plants or the 35S (CaMV35S) promoter carried by cauliflower mosaic virus, a plant virus, and the like.

Plants that are transformed by the introduction of recombinant DNA into the genome are not limited, but for the purpose of the present invention, they are preferably plants that can be used as a raw material for pulp, and include, for example, perennial woody plants that can be classified into genus Acacia, genus Abies, genus Albizia, genus Alnus, genus Carya, genus Cedrus, genus Eucalyptus, genus Ficus, genus Ginkgo, genus Gmelina, genus Larix, genus Laurelia, genus Liquidambar, genus Lithocarpus, genus Nothofagus, genus Picea, genus Pinus, genus Populus, genus Pseudotuga, genus Quercus, genus Tsuga, and genus Sequoia, as well as annual plants classified into genus Hibiscus and family Gramineae.

As methods for introducing genes into plants, there can be used an Agrobacterium-mediated gene transfer, the particle bombardment, electropolation, and the like.

In transformed plants obtained according to the present invention, the function of the endogenous 4CL gene is modified by the effect of the introduced recombinant DNA, which triggers increases or decreases in lignin content and changes in the molecular structure of lignin.

For enhanced productivity of pulp, it is exclusively preferred to significantly lower lignin content in transformed plants, and is more preferred to modify the molecular structure of lignin at the same time. To this end, it is preferred to lower the 4CL activity per total protein of the transformed plant to 50% or lower of the mean of that of the wild type plant.

Since the 4CL activity in the biological system is important for plant growth and the maintenance of various biological functions, a decreased activity, particularly in the leaf tissues responsible for photosynthesis or the epidermal tissues involved in protective reactions against pathogen attacks, may result in traits that are undesirable for survival of the transformed plants. Thus, it is preferred that the suppression of the 4CL activity by genetic manipulation is carried out only at the woody tissues or cells in the vicinity of the cambium of the stem (shoot) where lignin is vigorously synthesized but not at the other tissues or cells. In order to effect activity suppression at the xylem tissues or the cambial cells, it is preferred to construct recombinant DNA using a promoter of the gene that is specifically expressed in those xylem tissues or cells. Even when recombinant DNA that was constructed using a promoter constitutively expressed in many tissues and cells such as CaMV35S promoter, the expression of the transferred gene varies depending on each transformed plant. And thus, when a plurality of transformed plants that were created are analyzed, it is possible to obtain those transformed plants in which the 4CL activity is potently suppressed in the xylem tissues and the cambial cells of the stem than at the other tissues. When the nature of the DNA introduced into the genome is expected to adversely affect the growth characteristics etc. of transformed plants, creation of a plurality of transformed plants is followed by the investigation on the growth characteristics or the photosynthetic ability etc. of each plant so that industrially extremely useful transformed plants can be obtained that produce woody raw materials of which growth characteristics is similar to the wild type plants and which have excellent pulp productivity.

DESCRIPTION OF PREFERRED EMBODIMENTS

The procedures of the present invention will now be explained in more details with reference to the following Examples, but it is to be noted that the present invention is not limited by these Examples in any way.

EXAMPLE

[1] Isolation of cDNA Encoding 4CL

A portion of cDNA encoding the amino acid sequence of 4CL of *Eucalyptus globulus* was isolated by the polymerase chain reaction (hereinafter referred to as PCR) described below.

First, by comparing several of the amino acid sequences of 4CL elucidated for plant species other than Eucalyptus or of the amino acid sequences deduced from the cDNA for 4CL, two regions in the amino acid sequences of the 4CL protein that are highly conserved transcending the plant species. The amino acid sequences of these two regions are, from the amino-terminal end, GTTGLPKG and GWLHTGD. Then, since they were considered to be present on the CDNA of Eucalyptus 4CL, PCR primers were chemically synthesized in order to amplify by PCR a DNA fragment having a region flanked by CDNA regions each corresponding to these two amino acid sequences. The nucleotide sequences of the chemically synthesized primers are shown in SEQ ID NO: 3 and SEQ ID NO: 4.

Total RNA was extracted then from the hypocotyl and cotyledon derived from the seedling of *Eucalyptus globulus* using the RNeasy plant Mini Kit (manufactured by QIAGEN K.K.). Furthermore, using 1 µg of the total RNA extracted here, first strand cDNA was synthesized by the BcaBEST RNA PCR Kit (manufactured by Takara Shuzo Co., Ltd.). Total RNA extraction and cDNA synthesis were both performed according to the instructions attached to the kits.

Using first strand cDNA thus prepared as a template, PCR primers described in SEQ ID NO: 3 and SEQ ID NO: 4, magnesium sulfate at a final concentration of 25 mM, 2.5 units of Bca-Optimized Taq (manufactured by Takara Shuzo Co., Ltd.), 0.1 mM each of dATP, dTTP, dGTP, and dCTP, and the buffer solution (manufactured by Takara Shuzo Co., Ltd.) for PCR reaction attached to Bca-Optimized Taq were added to prepare a total of 100 µl reaction mixture. The PCR condition comprised, after treating the reaction mixture at 94° C. for 2 minutes, 30 cycles of "94° C. for 30 seconds, 50° C. for 1 minute, and 72° C. for 2 minutes."

The amplification of the desired DNA by PCR was confirmed by subjecting 10 µl of the reaction mixture after PCR to agarose gel electrophoresis using TAE buffer (pH 8.0, 40 mM Tris-acetate, 1 mM EDTA), staining the resolved DNA in the gel with ethidium bromide, and then visualizing under an ultra violet light. Furthermore, the PCR-amplified DNA was recovered from the agarose gel used in the above electrophoresis, and the DNA fragment was ligated to pCR2.1 vector attached to the TA Cloning Kit (manufactured by Invitrogen Corporation). After the ligation-treated vector was introduced into *E. coli* competent cells, it was incubated overnight at 37° C. on a LB agar medium containing 50 mg/l of Kanamycin and the same concentration of ampicillin, 20 mg/l of 5-bromo-4-chloro-3-indolyl-β-D-galactopyranoside, and 0.1 mM isopropyl-β-D-thio-galactopyranoside. From among the colonies that propagated on the agar medium by this procedure, white colonies were only picked up and were transferred to a separately prepared agar medium of the same composition to further propagate *E. coli* derived from each colony. *E. coli* clone thus prepared derived from each colony was each grown in a test tube containing 10 ml of a L broth solution, and then plasmid DNA carried by each clone was recovered from 32 independent *E. coli* clones.

Each plasmid DNA obtained in the above procedure was digested with restriction enzymes SacI, BamHI, HindIII, EcoRI, KpnI, and XbaI (manufactured by Takara Shuzo Co., Ltd.), and the digested DNA fragments thus obtained were fractionated by electrophoresis followed by visualization to identify how many DNAs were amplified in the above PCR. The band patterns on the electrophoresis gel revealed that at least 6 fragments are contained in the PCR-amplified DNA fragments.

Thus, the nucleotide sequences of these 6 fragments were partially determined. For the determination of the nucleotide sequence, a nucleotide sequence analyzer the Genetic Analyzer 310 of PE Applied Biosystems and the Big Dye Terminator Cycle sequencing FS Lady Reaction Kit of the same company were used. By subjecting the analyzed sequences to homology analysis with a genetic information processing software GENETYX (manufactured by Software Development Co., Ltd), the above 6 DNA clones were found to be roughly classified into two groups. Thus, one clone each was selected from the two groups, and the entire nucleotide sequences thereof were determined. The nucleotide sequences thus determined are shown in SEQ ID NO: 1 and SEQ ID NO: 2. The DNA fragments that have the sequence shown in SEQ ID NO: 1 and SEQ ID NO: 2 were each designated EG4CLPS3-1 and EG4CLPS3-3. *E. coli's* having the plasmid vectors pEG4CLPS3-1 and pEG4CLPS3-3 each carrying these DNAs were deposited with the Patent Microorganism Depository, the National Institute of Bioscience and Human Technology, Agency of Industrial Science and Technology, MITI, under the accession numbers FERM P-17367 and FERM P-17368. They were then transferred by the Depository to the Deposit of Microorganisms pursuant to the Budapest Treaty (International Deposition) under the accession numbers FERM BP-7011 and FERM BP-7012.

Then, based on the nucleotide sequence information for EG4CLPS3-1 and EG4CLPS3-3 thus obtained, a homology search was carried out for DNA having homology to the nucleotide sequences using the BLAST database software of the National Center for Biotechnology Information. The results revealed that the nucleotide sequences of EG4CLPS3-1 and EG4CLPS3-3 have a high homology with the base sequences of the 4CL gene or cDNA derived from other plant species such as parsley and potato, and thus these two clones were demonstrated to be part of cDNA encoding the 4CL of *Eucalyptus globulus*.

[2] Construction of Transformation Vectors

Using EG4CLPS3-1 and EG4CLPS3-3 obtained as described in the above Example [1], a sense 4CL gene and an antisense 4CL gene of which restriction maps are shown in FIG. 1 were constructed as follows:

First, the coding region of β-glucuronidase (GUS) gene on a plant transformation vector pBI121 (manufactured by CLONETECH Laboratories Inc.) was removed by digesting with two restriction enzymes SacI and SmaI. The ends of the digested vector were blunt-ended using the DNA Blunting Kit (manufactured by Takara Shuzo Co., Ltd.). Then the EG4CLPS3-1 and EG4CLPS3-3 fragments on pEG4CLPS3-1 and pEG4CLPS3-3, respectively, were each excised with a restriction enzyme EcoRI. After the both ends of the excised EG4CLPS3-1 and EG4CLPS3-3 fragments were blunt-ended using the DNA Blunting Kit (manufactured by Takara Shuzo Co., Ltd.) as described above, they were each ligated to the above blunt-ended pBI121 vector from which the GUS region had been removed. By this procedure, a total of 4 vectors were constructed in which the PCR-derived EG4CLPS3-1 and EG4CLPS3-3 have been inserted in the both forward and reverse orientations into a region flanked by the CaMV35S promoter and the terminator of the nopaline synthesis gene on pBI121. As used herein, the forward orientation refers to the direction of insertion of EG4CLPS3-1 and EG4CLPS3-3 so as to permit mRNA transcription from the coding strand of EG4CLPS3-1 and EG4CLPS3-3 by the CaMV35S promoter, and the reverse orientation refers to the direction of insertion of EG4CLPS3-1 and EG4CLPS3-3 so as to permit MRNA transcription from the nonsense strand by the CaMV35S promoter. The vectors (vectors having the sense 4CL gene) having a recombinant DNA in which EG4CLPS3-1 or EG4CLPS3-3 has been inserted in the forward orientation to the CaMV35S promoter in the T-DNA region were designated pSEG3-1 and pSEG3-3, respectively, and the vectors (vectors having the antisense 4CL gene) having a recombinant DNA in which EG4CLPS3-1 or EG4CLPS3-3 has been inserted in the reverse orientation to the CaMV35S promoter in the T-DNA region were designated pAEG3-1 and pAEG3-3, respectively, and the structures of T-DNA regions are shown in FIG. 1.

[3] Gene transfer into Eucalyptus Using a Transformation Vector

Using pBI121, PSEG3-1, pSEG3-3, pAEG3-1, and pAEG3-3 of which structures are shown in FIG. 1, Eucalyptus was transformed as follows:

First, each of the above 5 vectors was separately retained in *Agrobacterium tumefaciens* strain LBA4404. For introduction of each vector into *A. tumefaciens*, a total of three stains comprising any one of *E. coli* strain HB101 carrying each transformation vector, *E. coli* strain HB101 carrying plasmid vector pRK2013, and *A. tumefaciens* LBA4404 were mixed and subjected to a stationary culture in a tripartite conjugal transfer. When *A. tumefaciens* obtained by these procedures is used in a transformation experiment, a cell suspension was used that was prepared by suspending the cells obtained by culturing in the L broth (including 1 g/l BACTO TRYPTONE, 0.5 g/l BACTO YEAST EXTRACT, 0.5 g/l sodium chloride, 50 mg/l kanamycin sulfate) for 12 hours prior to the start of the experiment in the Schenk & Hildebrandt.(SH) medium (Schenk and Hildebrandt, Can. J. Bot., vol. 50, 199–204, 1972).

Tissue sections used in the transformation experiment were prepared as follows: Fist, seeds of *Eucalyptus globulus* produced in Chile in the South America were treated in 70% ethanol (manufactured by Wako Pure Chemicals Industries, Ltd.) and 1% sodium hypochlorite solution (manufactured by Wako Pure Chemicals Industries, Ltd.) for 5 minutes and 20 minutes, respectively, to sterilize the seed surface, and then washed for 20 minutes with sterilized distilled water. The thus surface-sterilized seeds were placed on the Murashige & Skoog medium (Physiol. Plantarum., vol 15, 473–479, 1962) solidified using 0.8% agar powder, and cultured at a temperature condition of 25 (±3)° C. and a light irradiation condition of "an illumination of 6000 lux for 16 hours and 8 hours in the dark per day cycle." By this procedure, seedlings about 1–5 cm long were obtained 2 weeks later.

From the seedlings obtained, the hypocotyl portion was excised about 5 mm in length using a scalpel under a sterile condition, was then immersed in a cell suspension of *A. tumefaciens* strain LBA4404 carrying each vector for 2 minutes. After the extra suspension attached to the hypocotyl section was blotted on a filter paper, it was placed on the SH medium solidified with 0.25% gellan gum (manufactured by Wako Pure Chemicals Industries, Ltd.) and cultured at 25 (±3)° C. in the dark for 6 days. To the SH medium used, benzyladenine (BA; manufactured by Wako Pure Chemicals Industries, Ltd.) and naphthalene acetate (NAA; manufactured by Wako Pure Chemicals Industries, Ltd.) as plant hormones had been added at a final concentration of 0.15 mg/l and 0.05 mg/l, respectively.

The hypocotyl section subjected to a gene transfer treatment as described above was transferred to the SH medium containing 0.15 mg/l of BA, 0.05 mg/l of NAA, 500 mg/l of carbenicillin sodium salt (manufactured by Wako Pure Chemicals Industries, Ltd.) and 0.25% of gellan gum, and was further cultured for one week. The temperature condition at the time of culturing was set at 25 (±3)° C. and the light irradiation condition at "an illumination at 6000 lux for 16 hours and 8 hours in the dark per day cycle."

After culturing for one week, the above hypocotyl section was transfected to the SH medium containing 0.15 mg/l of BA, 0.05 mg/l of NAA, 500 mg/l of carbenicillin sodium salt and 0.25% of gellan gum, and was continuously cultured under the temperature condition of 25 (±3)° C. and the light irradiation condition of "an illumination at 6000 lux for 16 hours and 8 hours in the dark per day cycle." The above hypocotyl section was subcultured in a fresh medium of the same composition every two weeks until shoots started to differentiate.

Part of the hypocotyl section tested by these procedures gradually changed its morphology accompanied by callus formation, and shoots started to differentiate 6 months after the transformation treatment. The differentiated shoot was dissected from the callus with a scalpel and was transplanted to the SH medium containing 50 mg/l kanamycin sulfate, 1.0 mg/l indole butyric acid (IBA), and 0.25% gellan gum, subjected to a radication treatment for one week, and was transferred to the SH medium containing 50 mg/l kanamycin sulfate and 0.25% gellan gum to facilitate radication.

The transformed young plant rooted by the above procedure was cultured on the SH medium (containing 50 kanamycin sulfate and 0.25% gellan gum) without the addition of plant hormones for 2 months after radication, and then transplanted to a pot with soils to continue culturing.

For the transformed plants obtained by the above procedure, presence of gene transfer in each plant was investigated by the Southern hybridization method and PCR, and transfer of the gene (T-DNA) was confirmed for all plants tested.

Six per each vector or a total of 30 transformed plants that underwent transfer of T-DNA on each vector by the above method were selected and the culturing was further continued. The 30 plants were cultured in a green house for 3 years form the day they were first implanted in the soil, and then subjected to the experiment below.

At the time point of 3 years of growing, there were no significant differences observed in the amount of growth of the plants (a total of 24 plants) into which each antisense gene or sense gene was introduced compared to the wild type plants (6 plants that were transformed using pBI121).

[4] Measurement of the 4CL Activity in the Transformed Eucalyptus Plants

Crude enzyme was prepared from the stem tissue of the transformed Eucalyptus plants obtained by the procedure described in Example [3], and was used to determine the 4CL activity as follows:

First, about 5 g of the stem tissue was prepared from each transformed Eucalyptus plant, which was then homogenized in a mortar and pestle in the presence of liquid nitrogen. The pulverized tissue was transferred to a centrifuge tube, to which 10 ml of the buffer solution (200 mM Tris-HCl, pH 8.0, 0.1% mercaptoethanol) was added, and which was placed on ice for 30 minutes to extract crude enzyme from the homogenized stem tissue. Then, the above extract was centrifuged at 5500×g for 5 minutes, and the supernatant was transferred to another centrifuge tube. To the supernatant was added ammonium sulfate (manufactured by Wako Pure Chemicals Industries, Ltd.) to a final concentration of 30%, which was then placed on ice for 30 minutes. The above solution was centrifuged at 5500×g for 5 minutes, and the resultant supernatant was transferred to another centrifuge tube. To the supernatant was added ammonium sulfate to a final concentration of 75%, which was then placed on ice for 30 minutes. Protein that deposited during this procedure was precipitated by centrifuging at 5500×g for 5 minutes. After the precipitate was dissolved in 0.5 ml of the buffer (200 mM Tris-HCl, pH 8.0, 0.1% mercaptoethanol), it was desalted overnight using a cellophane dialysis membrane, and the solution after desalting was designated a crude enzyme solution. The amount of protein contained in each enzyme solution was determined using the Bio-Rad Protein Assay kit (manufactured by Nippon Bio-Rad Laboratories, K.K.) using bovine serum albumin as a standard protein.

In order to determine the 4CL activity using the above crude enzyme solution, a reaction mixture (200 mM Tris-HCl, 1 mM dithiothreitol, 500 mM p-coumaric acid, 5 mM magnesium sulfate, 5 mM ATP, 300 mM coenzyme A, the crude enzyme solution) was prepared at total volume of 1 ml, and was reacted at 30° C. for 5 minutes. In addition, an experiment using a heat-inactivated crude enzyme solution was also carried out as a blank. After the reaction, absorbance of the reaction mixture at 333 nm was determined using the solution of the above blank experiment as a reference to obtain a 4CL activity value contained in the crude enzyme solution using an extinction coefficient in a previous publication (Knoblock and Hahlbrock, Eur. J. Biochem., Vol 52, 311–320, 1965).

The results of the 4CL activity determination experiment using the crude enzyme derived from each transformed Eucalyptus plant are shown in Table 1. In making Table 1, the transformed plants were numbered in a decreasing order of the activity value. From Table 1, it is evident that the mean 4CL activity value of 6 transformed plants transformed with pBI121 is about 317 pkat/mg protein, whereas in plants transformed using pSEG3-1, pSEG3-3, pAEG3-1 and pAEG3-3 each of the above mean value decreased to about 4.7% (SEG3-1-6), 5.6% (SEG3-3-6), 3.5% (AEG3-1-6), and 6.6% (AEG3-3-6) when compared for the plants with the lowest activity. These results indicated that the introduction of the sense 4CL gene and the antisense 4CL gene enables to obtain transformed plants having a suppressed 4CL activity and normal growth.

[5] Measurement of Lignin Content in the Transformed Eucalyptus Plants

From the stem of transformed plants used for measurement of the 4CL activity in the above Example [4] wood meal was prepared, and the wood meal was used to determine lignin content therein. The measurement was performed in accordance with the Japanese Industrial Standard (JIS) P8008, and the results are shown in Table 1.

It is evident from Table 1 that the mean value of lignin content of 6 transformed plants transformed with pBI121 is about 22.4%, whereas in plants transformed using pSEG3-1, pSEG3-3, pAEG3-1 and pAEG3-3 each of the above mean value decreased to about 64% (SEG3-1-6), 63% (SEG3-3-6), 65% (AEG3-1-6), and 70% (AEG3-3-6) when compared for the plants with the lowest content. These results indicated that the introduction of the sense 4CL gene and the antisense 4CL gene enables to lower lignin content in each plant.

[6] Pulping Test Using Wood Chips Derived from Transformed Eucalyptus Plants

From among the transformed plants that exhibited a decreased 4CL activity, 4 plants (plant number SEG3-1-6, SEG3-3-6, AEG3-1-6, and AEG3-3-6) were selected, and wood chips were prepared from them for the pulping test that was carried out as described below.

First, the stem was cut from the above 4 plants, the bark thereof was peeled off and then cut and chipped using a chipper. These wood chips were dried at room temperature for 2 weeks, and then used as samples. Each of the chips was aliquoted at an amount equivalent to 300 g of the absolute dry weight, placed into a 4-liter autoclave, to which a cook white liquor was added at a required amount. The cook reaction condition was set at a volume ratio of the chips and the cook white liquor 1:4, an effective alkali (EA) addition percentage 9.5%, the time to the highest temperature 1 hour, the highest temperature 170° C., and the retention time of the highest temperature 43 minutes. As used herein, the effective alkali refers to the sum of half the amount of $Na_2S$ and the total amount of NaOH contained in the cook white liquor in terms of NaO, and is expressed in a weight ratio (%) to the absolute dry weight of the chips used in cooking.

Pulp obtained after the cooking reaction performed as described above was washed in pure water, sieved with a 8/1000 inch flat screen, and the fraction that passed through the screen was designated the selected pulp. The yield of the selected pulp was expressed in a weight ratio (%) versus the wood chips used for cooking. Part of the selected pulp was used to determine a kappa number of the pulp in accordance with the Japanese Industrial Standard (JIS) P8211.

The results of this Example are summarized in Table 2.

Comparative Example 1

In a cooking reaction condition similar to that in Example [6], a pulping test was carried out in which wood chips prepared from a total of 6 plants comprising 2 Eucalyptus plants (plant numbers 121-1 and 121-6) that were transformed using pBI121, and 4 plants (plant numbers SEG3-1-1, SEG3-3-1, AEG3-1-1, and AEG3-3-1) but exhibited no decrease in the 4CL activity were used. The results are shown in Table 2.

The results in Table 2 indicate that in the pulping test under the condition of an EA addition ratio of 9.5% the amount of pulp obtained from the 4 plants that exhibited decreased levels of 4CL activity is increased by 10% or more compared to the mean of those from the 6 plants in which the 4CL activity is about the same level as the wild type plants, and that the kappa number which is an index of residual lignin content in the pulp is mostly lower in the plants that exhibited decreased levels of 4CL activity.

[7] Pulping Test Using Wood Chips Derived from Transformed Eucalyptus Plants

A pulping test was carried out by changing the EA addition ratio to 10.0% under the condition of Example [6] and in a similar cooking reaction condition to [6] for the others using wood chips obtained from 4 transformed plants (plant numbers SEG3-1-6, SEG3-3-6, AEG3-1-6, and AEG3-3-6) that exhibited decreased levels of 4CL activity The results are shown in Table 2 as described above.

Comparative Example 2

A pulping test was carried out in a similar manner to Example [7] for wood chips prepared from each of a total of 6 plants comprising 2 Eucalyptus plants (plant numbers 121-1 and 121-6) that were transformed with pBI121 and 4 transformed plants (plant numbers SEG3-1-1, SEG3-3-1, AEG3-1-1, and AEG3-3-1) that were transformed with pSEG3-1, pSEG3-3, pAEG3-1, and pAEG3-3, respectively, but exhibited no decrease in the 4CL activity. The results are shown in Table 2 as described above.

The results in Table 2 indicate that in the pulping test under the condition of an EA addition ratio of 10.0% the amount of pulp obtained from the 4 plants that exhibited decreased levels of 4CL activity is increased by 10% or more compared to the mean of those from 6 plants in which the 4CL activity is about the same level as the wild type plants, and that the kappa number which is an index of residual lignin content in the pulp is mostly lower in the 4 plants that exhibited decreased levels of 4CL activity.

EFFECT OF THE INVENTION

From the foregoing, the present invention enabled the creation of transformed plants that produce woody raw materials having excellent pulp productivity.

TABLE 1

4CL activity values and Lignin content in the cell wall of each transformed plant

| Vector used for transformation | Plant No. | 4Cl activity (pkat/mg of protein) | Lignin content per unit weight of wood meal (%) |
|---|---|---|---|
| pBI121 | 121-1 | 368 | 23.5 |
| | 121-2 | 353 | 22.5 |
| | 121-3 | 321 | 23.1 |
| | 121-4 | 299 | 20.1 |
| | 121-5 | 289 | 24.3 |

TABLE 1-continued

| | 121-6 | 270 | 20.8 |
|---|---|---|---|
| PSEG3-1 | SEG3-1-1 | 320 | 22.2 |
| | SEG3-1-2 | 289 | 22.4 |
| | SEG3-1-3 | 69 | 18.2 |
| | SEG3-1-4 | 53 | 17.9 |
| | SEG3-1-5 | 34 | 16.1 |
| | SEG3-1-6 | 15 | 14.3 |
| pSEG3-3 | SEG3-3-1 | 302 | 24.3 |
| | SEG3-3-2 | 275 | 23.8 |
| | SEG3-3-3 | 261 | 23.9 |
| | SEG3-3-4 | 99 | 18.1 |
| | SEG3-3-5 | 51 | 17.5 |
| | SEG3-3-6 | 18 | 14.1 |
| pAEG3-1 | AEG3-1-1 | 366 | 22.8 |
| | AEG3-1-2 | 75 | 18.3 |
| | AEG3-1-3 | 65 | 18.3 |
| | AEG3-1-4 | 62 | 18.1 |
| | AEG3-1-5 | 51 | 17.6 |
| | AEG3-1-6 | 11 | 13.9 |
| pAEG3-3 | AEG3-3-1 | 345 | 22.6 |
| | AEG3-3-2 | 279 | 24.9 |
| | AEG3-3-3 | 221 | 21.8 |
| | AEG3-3-4 | 199 | 22.4 |
| | AEG3-3-5 | 41 | 16.9 |
| | AEG3-3-6 | 21 | 15.6 |

Results of the cooking test using wood chips derived from transformed plants

| Plant No. | Presence of decreased 4CL activity | When the effective alkali is 9.5% | | When the effective alkali is 10% | |
|---|---|---|---|---|---|
| | | Kappa number | Yield of selected pulp per weight of wood chips (%) | Kappa number | Yield of selected pulp per weight of wood chips (%) |
| 121-1 | No | 22.5 | 50.1 | 20.1 | 54.6 |
| 121-6 | No | 23.1 | 51.2 | 20.9 | 55.1 |
| SEG3-1-1 | NO | 22.9 | 51 | 19.8 | 53.1 |
| SEG3-3-1 | No | 24 | 50.9 | 19 | 54.2 |
| AEG3-1-1 | No | 21.2 | 49.9 | 21.3 | 55.6 |
| AEG3-3-1 | No | 24.6 | 51.5 | 19.1 | 53.7 |
| SEG3-1-6 | Yes | 17.1 | 59.1 | 15.2 | 61.2 |
| SEG3-3-6 | Yes | 16.9 | 60.1 | 13.8 | 59.9 |
| AEG3-1-6 | Yes | 16.5 | 58.2 | 14.2 | 62.3 |
| AEG3-3-6 | Yes | 17.5 | 59.4 | 15.1 | 61.8 |

What is claimed is:

1. A cDNA molecule consisting of SEQ ID NO:2.

2. A recombinant DNA molecule comprising SEQ ID NO:2, inserted in the antisense direction into a DNA molecule comprising a promoter sequence and a terminator sequence.

3. A transformed plant comprising a plant genome comprising the recombinant DNA according to claim 2.

4. A transformed plant according to claim 3 in which said plant is a woody plant.

5. A transformed plant according to claim 4 in which said woody plant is a plant of genus Eucalyptus.

6. A cell obtained from a transformed plant according to claim 3.

7. A seed obtained from a transformed plant according to claim 3.

8. A fruit obtained from a transformed plant according to claim 3.

9. A method of modifying the content of lignin in a plant comprising introducing a recombinant DNA according to claim 2 into the genome of a plant to change the production level of enzymes having a 4-coumarate:coenzyme A ligase activity, thereby modifying the content of lignin present in the cell wall of a transformed plant.

* * * * *